(12) United States Patent
Flintrop et al.

(10) Patent No.: US 11,185,355 B2
(45) Date of Patent: Nov. 30, 2021

(54) GUIDE SLEEVE FOR FINE AXIAL ADJUSTABILITY OF A FIXATION MEMBER, AND RELATED SYSTEMS AND METHODS

(71) Applicant: DEPUY SYNTHES PRODUCTS, INC., Raynham, MA (US)

(72) Inventors: Andrew Flintrop, West Chester, PA (US); Thomas Keyer, West Chester, PA (US); Stanley Kmiec, Jr., Morgantown, PA (US); Alexandra Sibole, Seattle, WA (US); Dana Pappalardo, Landenberg, PA (US); David Cowens, West Chester, PA (US); Joshua McManus, Downingtown, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 186 days.

(21) Appl. No.: 16/531,747

(22) Filed: Aug. 5, 2019

(65) Prior Publication Data

US 2021/0038268 A1 Feb. 11, 2021

(51) Int. Cl.
 *A61B 17/72* (2006.01)
 *A61B 17/16* (2006.01)
 *A61B 17/17* (2006.01)

(52) U.S. Cl.
 CPC ........ *A61B 17/7233* (2013.01); *A61B 17/164* (2013.01); *A61B 17/1721* (2013.01); *A61B 17/1717* (2013.01); *A61B 17/1725* (2013.01)

(58) Field of Classification Search
 CPC ..... A61B 17/17; A61B 17/1721; A61B 17/16; A61B 17/164; A61B 17/72; A61B 17/7233
 See application file for complete search history.

(56) References Cited

U.S. PATENT DOCUMENTS

| 3,927,574 A | 12/1975 | Rice | |
| 6,379,360 B1 * | 4/2002 | Ackeret | ............. A61B 17/1725 606/60 |

(Continued)

FOREIGN PATENT DOCUMENTS

DE 29804268 U1 5/1998

OTHER PUBLICATIONS

TFN-ADVANCED@ Proximal Femoral Nailing System (TFNA) Surgical Technique guide, 91 pages.

*Primary Examiner* — Christopher J Beccia
(74) *Attorney, Agent, or Firm* — BakerHostetler

(57) ABSTRACT

A guide sleeve for use in anchoring a fixation member to an intramedullary nail and to bone includes a sleeve body that is elongate along a central axis and has an internal surface that defines a bore extending along the central axis to a distal end of the sleeve body. The sleeve body also defines a plurality of guide channels that are each recessed radially outwardly from the internal surface and each include a helical proximal portion and a linear distal portion that extends from the helical proximal portion toward the distal end. The linear distal portion is parallel with the central axis. The guide channels are configured to receive respective complimentary followers of an instrument for driving the fixation member through the bore and subsequently through the intramedullary nail and into the bone.

20 Claims, 9 Drawing Sheets

(56) References Cited

U.S. PATENT DOCUMENTS

| | | | |
|---|---|---|---|
| 8,152,807 B2* | 4/2012 | Edwards | A61B 17/7225 606/62 |
| 8,808,293 B2 | 8/2014 | Buettler et al. | |
| 2003/0074005 A1 | 4/2003 | Roth et al. | |
| 2018/0140310 A1* | 5/2018 | Machamer | A61B 17/1725 |
| 2018/0171721 A1 | 6/2018 | Domani et al. | |

* cited by examiner

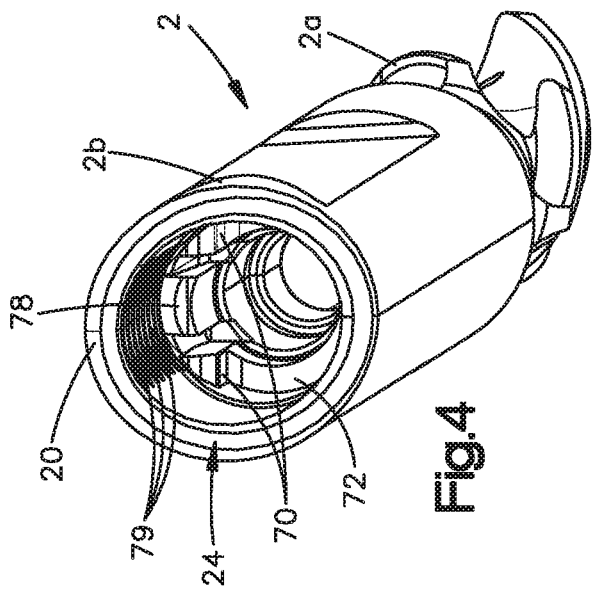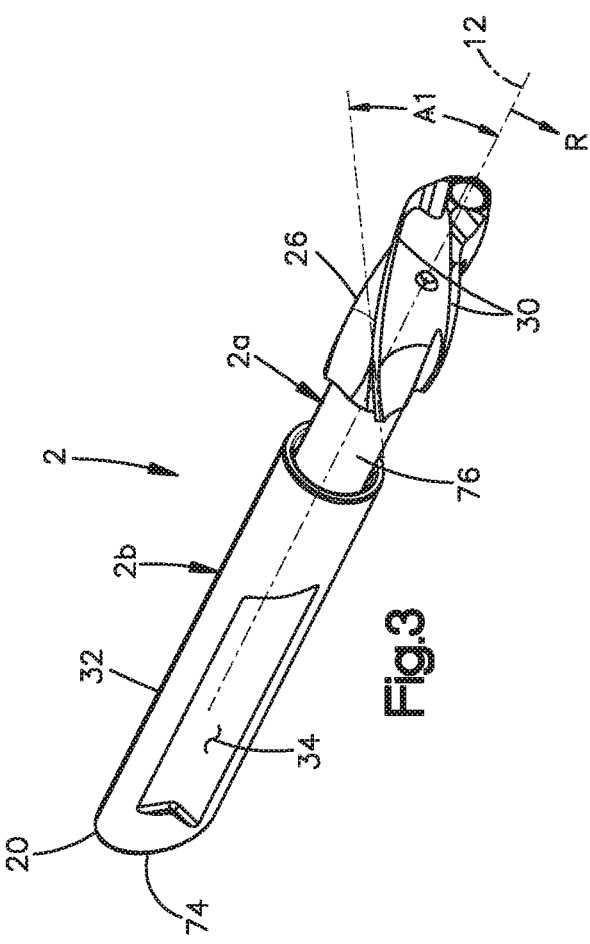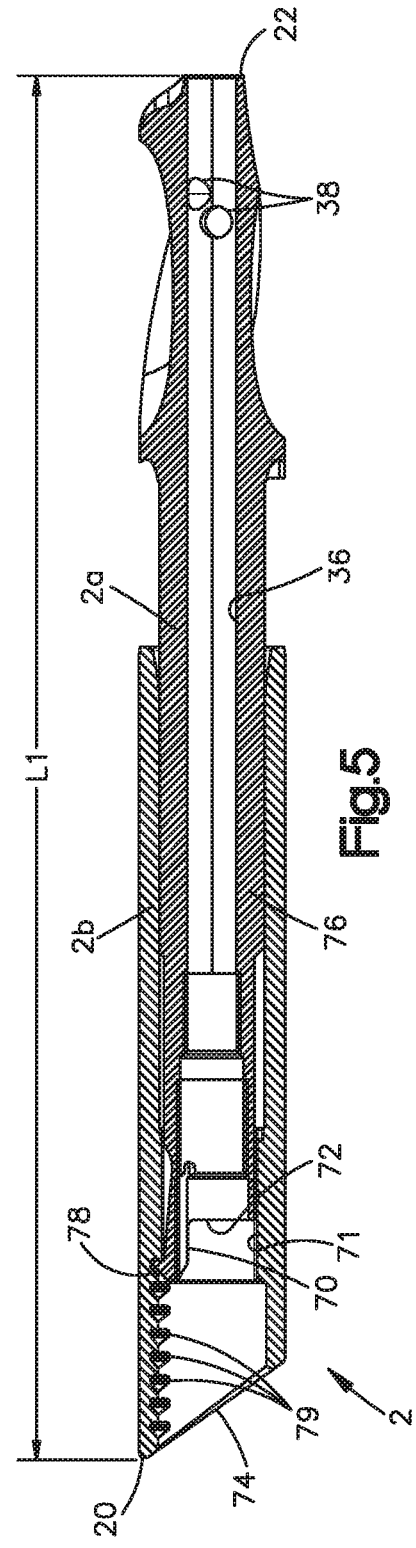

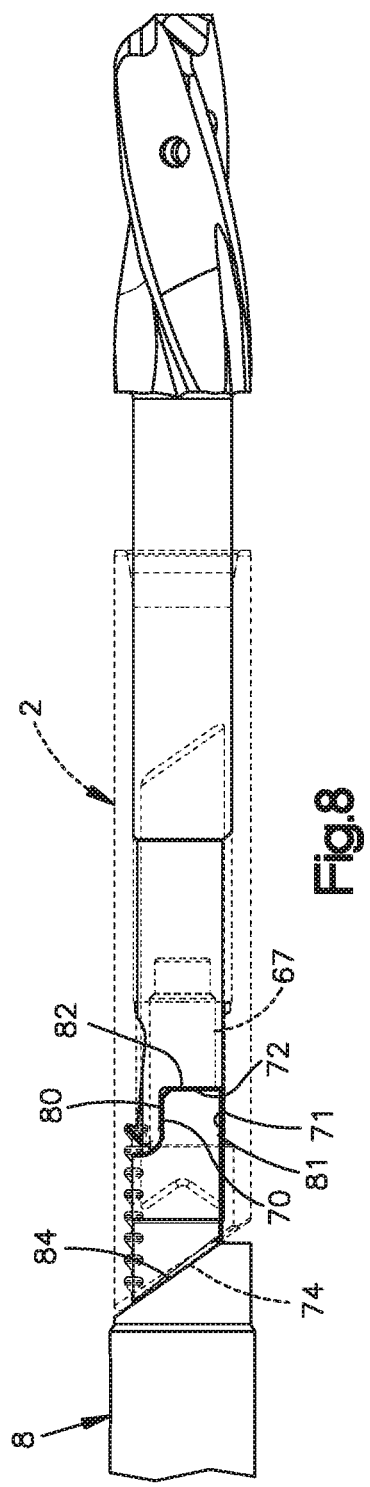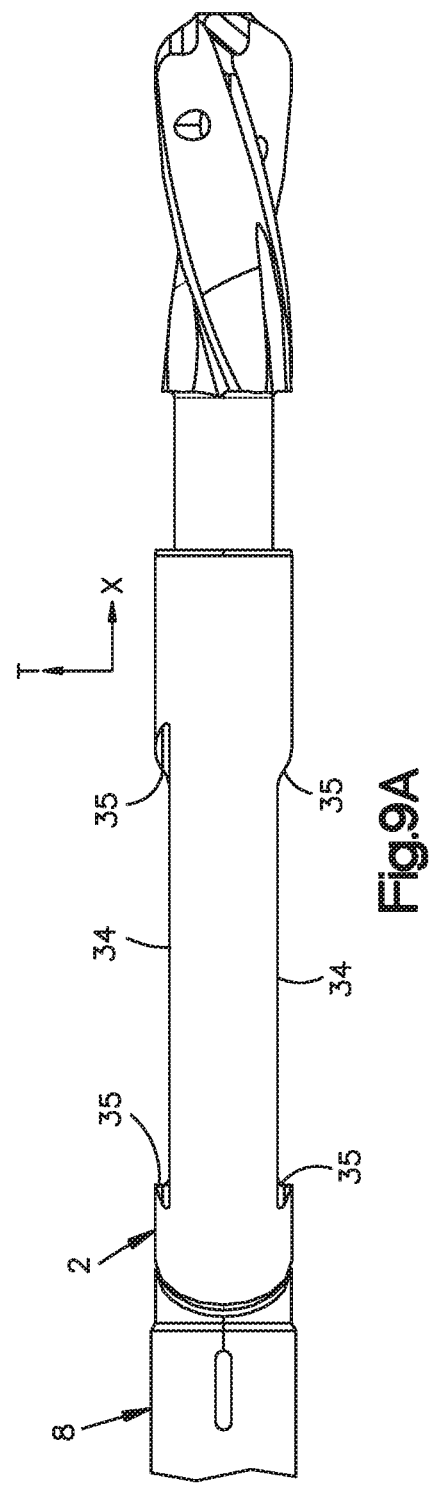

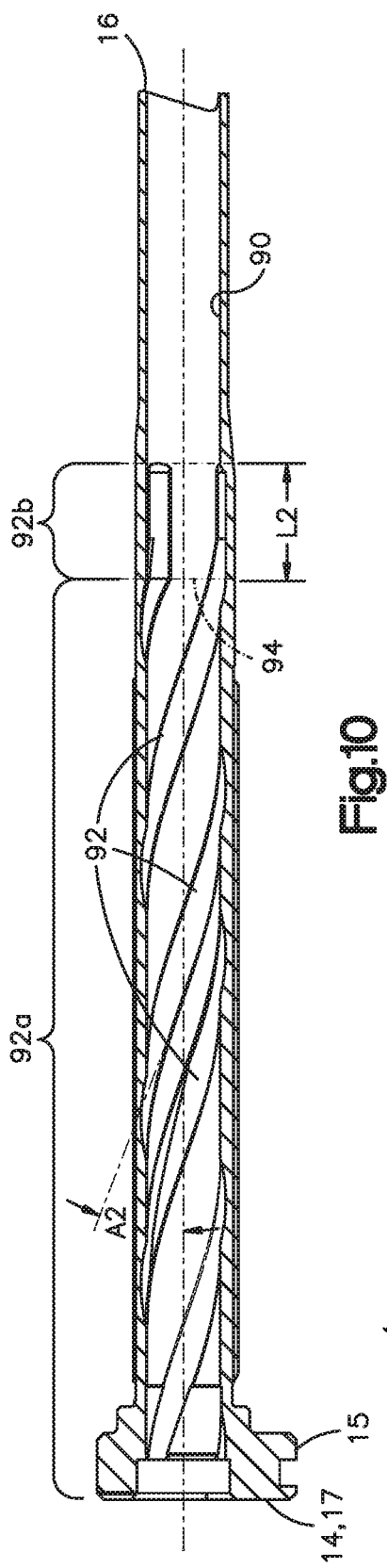
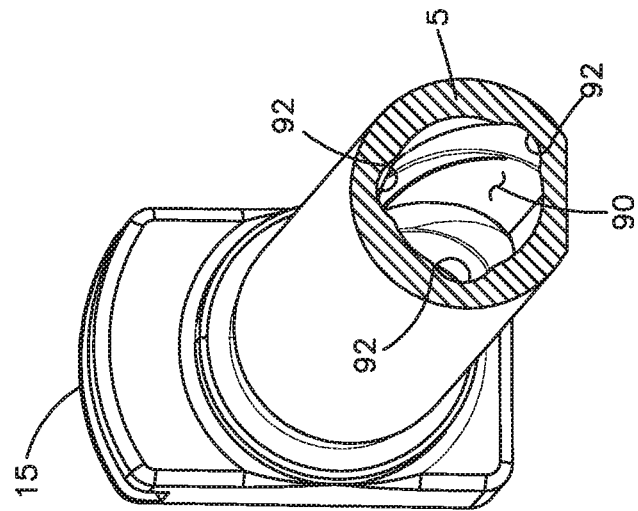
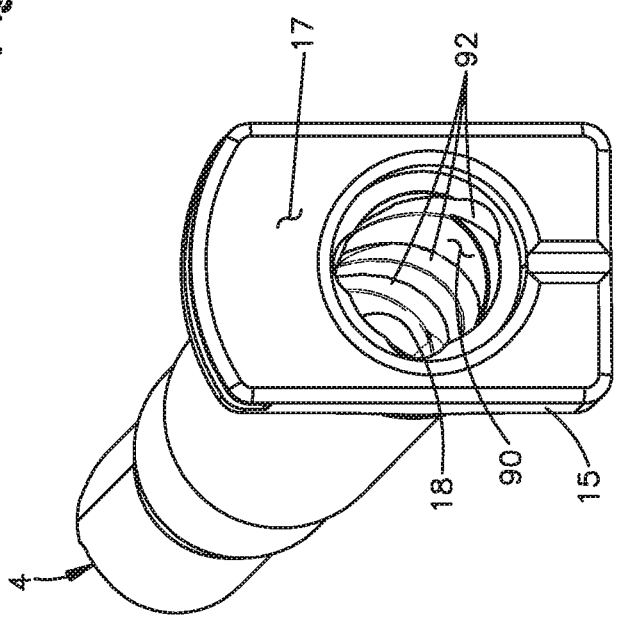

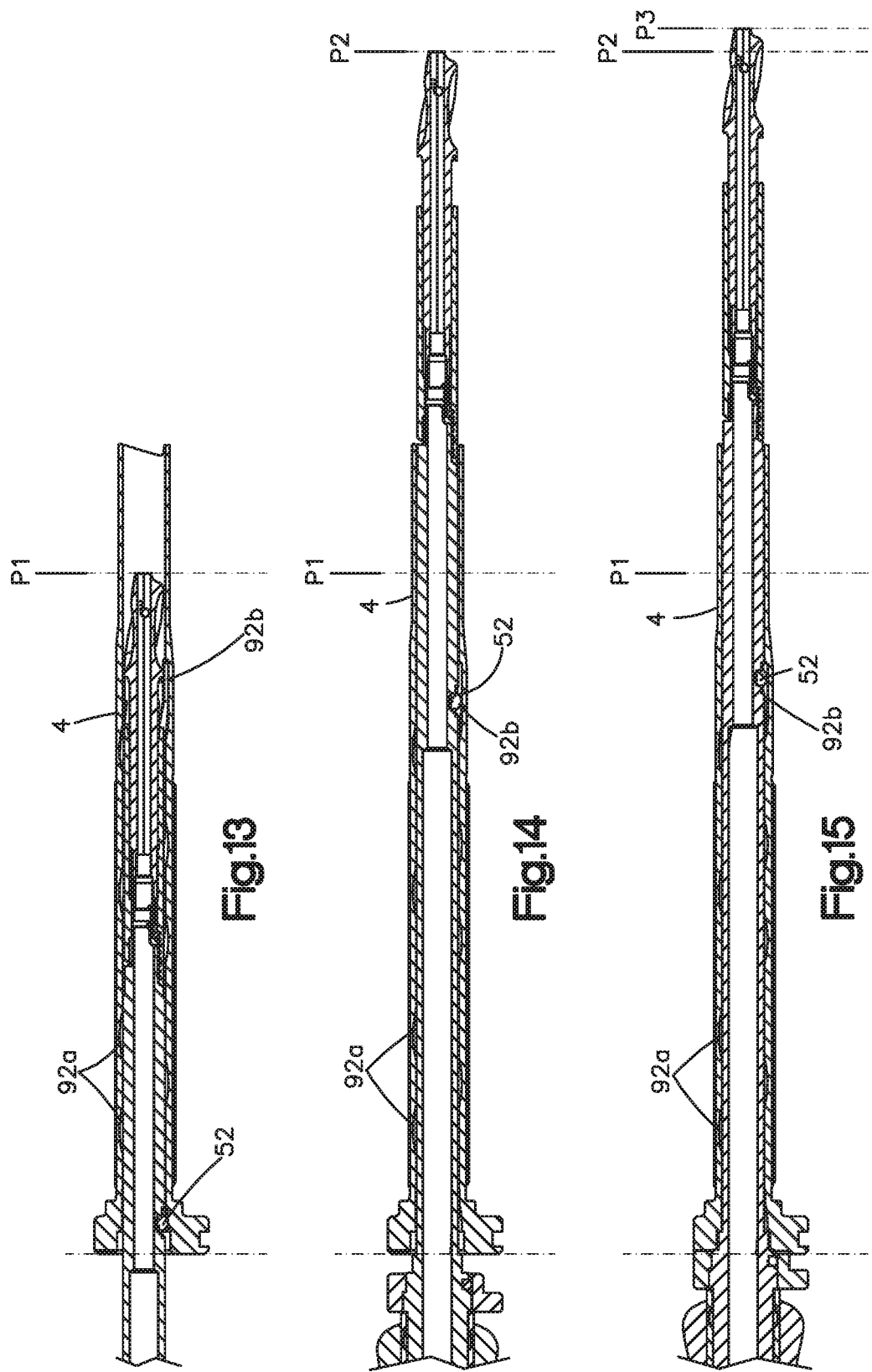

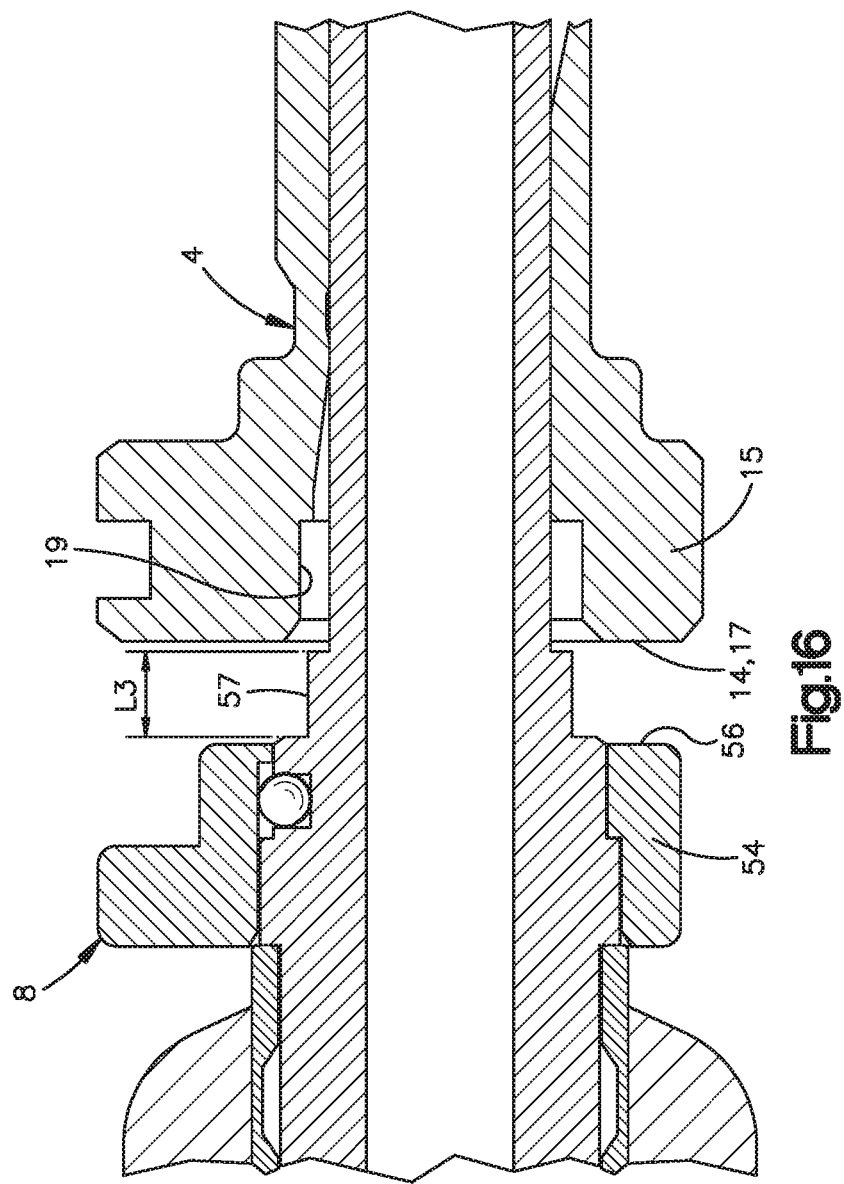

GUIDE SLEEVE FOR FINE AXIAL ADJUSTABILITY OF A FIXATION MEMBER, AND RELATED SYSTEMS AND METHODS

TECHNICAL FIELD

The present invention relates to devices for providing precise control of the axial advancement of a fixation member within bone, as well as to systems and methods related to intramedullary nailing techniques.

BACKGROUND

Fractures are often treated with screws or other fixation devices inserted into or through a bone to stabilize fractured portions thereof once they have been brought into corrective alignment. Trochanteric bone fixation treatments comprise the insertion of an intramedullary nail into a medullary cavity of a bone and a subsequent insertion of a bone fixation nail into a condylar portion of the bone at an angle relative to the intramedullary nail (i.e., along an axis of the femoral neck and center of the femoral head).

SUMMARY

According to an embodiment of the present disclosure, a bone fixation system for use with an intramedullary nail includes a guide sleeve elongate along a central axis and having a sleeve body configured to be held in position relative to a bone by an aiming arm. The sleeve body includes an internal surface that defines a bore extending along the central axis to a distal end of the sleeve body. The sleeve body defines at least one guide channel that is recessed radially outwardly from the internal surface and includes a helical proximal portion and a linear distal portion, wherein the linear distal portion extends from the helical proximal portion toward the distal end and is parallel with the central axis. The system includes a fixation member configured to extend through the bore of the guide sleeve. The fixation member has a proximal mount and a distal head spaced from the proximal mount in a distal direction. The distal head has a helical structure configured to engage bone. The system includes an instrument having an elongate portion that includes a distal mount configured to couple with the proximal mount of the fixation member, such that, when coupled, the instrument is configured to advance the fixation member through the bore of the guide sleeve, the elongate portion having an outer surface and at least one protrusion extending radially outward from the outer surface, wherein the at least one protrusion is configured to extend within and follow the at least one guide channel as the elongate portion advances through the bore of the guide sleeve so as to control an axial position of the fixation member relative to the guide sleeve.

According to another embodiment of the present disclosure, a guide sleeve for use in anchoring a fixation member to an intramedullary nail and to bone includes a sleeve body that is elongate along a central axis and has an internal surface that defines a bore extending along the central axis to a distal end of the sleeve body. The sleeve body also defines a plurality of guide channels that are each recessed radially outwardly from the internal surface and each include a helical proximal portion and a linear distal portion that extends from the helical proximal portion toward the distal end. The linear distal portion is parallel with the central axis. The guide channels are configured to receive respective complimentary followers of an instrument for driving the fixation member through the bore and subsequently through the intramedullary nail and into the bone.

According to an additional embodiment of the present disclosure, a method of affixing an intramedullary nail within an intramedullary canal of a bone includes advancing a guide sleeve through a complimentary aperture in an aiming arm attached to the intramedullary nail until a distal end of the guide sleeve contacts an outer cortex of the bone along a trajectory defined along a central axis of the guide sleeve such that the central axis intersects a lateral channel of the intramedullary nail. The method includes inserting an instrument through a central bore of the guide sleeve such that external followers of the instrument extend within respective channels defined within an internal surface of the guide sleeve within the central bore, wherein proximal portions of the channels extend helically along the internal surface. The method includes impacting a proximal surface of the instrument, thereby moving the external followers along the proximal portions of the channels, thereby simultaneously 1) advancing a fixation member, coupled to a distal end of the instrument, axially along the central axis, and 2) rotating the fixation member about the central axis, wherein the impacting step causes a helical structure of the fixation member to advance through the lateral channel of the intramedullary nail and subsequently engage bone. The method includes further impacting the proximal surface, thereby moving the external followers into distal linear portions of the channels that extend parallel with the central axis, thereby advancing the fixation member axially into further engagement with the bone substantially without rotating the fixation member about the central axis.

BRIEF DESCRIPTION OF THE DRAWINGS

The foregoing summary, as well as the following detailed description of illustrative embodiments of the present application, will be better understood when read in conjunction with the appended drawings. For the purposes of illustrating the structures of the present application, there is shown in the drawings illustrative embodiments. It should be understood, however, that the application is not limited to the precise arrangements and instrumentalities shown. In the drawings:

FIG. 3 is a perspective view of a fixation member of the locking assembly illustrated in FIG. 2;

FIG. 4 is a perspective view of the fixation member illustrated in FIG. 3;

FIG. 5 is a sectional side view of the fixation member illustrated in FIGS. 3 and 4;

FIG. 8 is a side plan view of the fixation member illustrated in FIGS. 2 through 5 mounted to the distal mount illustrated in FIGS. 6 and 7;

FIG. 9A is a bottom plan view of the fixation member illustrated in FIG. 8;

FIG. 10 is a sectional side view of the guide sleeve illustrated in FIG. 2;

FIG. 11 is a rear perspective view of the guide sleeve illustrated in FIG. 10;

FIG. 12 is an end sectional view of the guide sleeve illustrated in FIGS. 10 and 11;

FIG. 13 is a sectional side view of the fixation member of FIGS. 2 through 5 positioned within the guide sleeve at a first position;

FIG. 14 is a sectional side view of the fixation member extending from the guide sleeve at a second position;

FIG. 15 is a sectional side view of the fixation member extending from the guide sleeve at a third position; and FIG. 16 is a sectional side view of a portion of an insertion instrument according to an additional embodiment of the present disclosure engaged with a guide sleeve, wherein the insertion instrument has a boss that provides visual indicia of an axial location of the fixation member relative to the guide sleeve.

DETAILED DESCRIPTION OF ILLUSTRATIVE EMBODIMENTS

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The terms "approximately" and "substantially", as used herein with respect to dimensions, angles, and other geometries, takes into account manufacturing tolerances. Further, the terms "approximately" and "substantially" can include 10% greater than or less than the stated dimension or angle. Further, the terms "approximately" and "substantially" can equally apply to the specific value stated.

Figure 1:
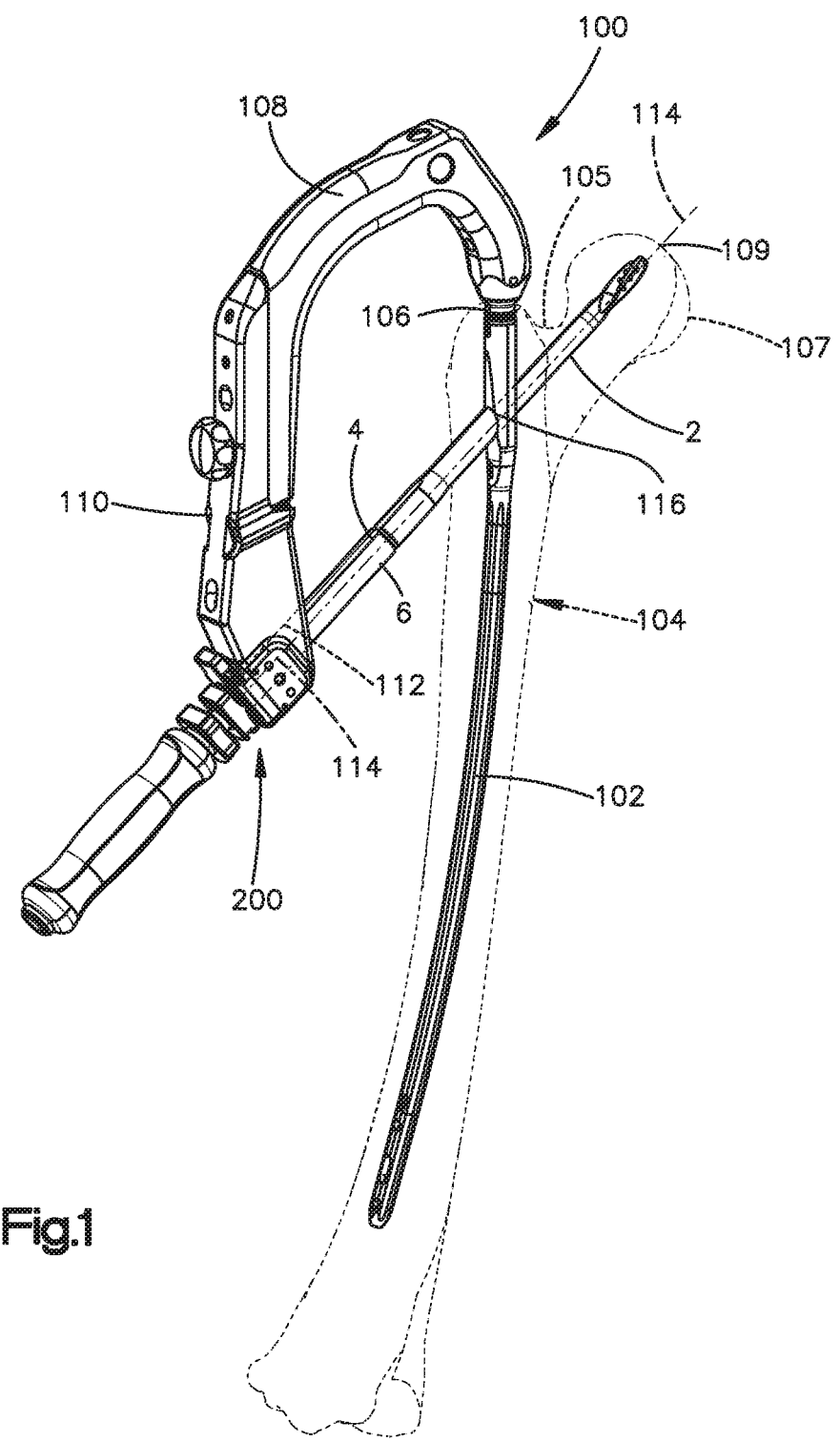
FIG. 1 is a perspective view of a bone fixation system that includes an intramedullary nail, according to an embodiment of the present disclosure.

Referring now to FIG. 1, an exemplary embodiment of a bone fixation system 100 includes an intramedullary nail 102 for insertion within an intramedullary canal of a bone 104. In the illustrated embodiment, the bone 104 is a femur, although it should be appreciated that the bone fixation system 100 can be adapted for use with other bones, as needed. A proximal end 106 of the intramedullary nail 102 can be coupled to an insertion handle 108, which is configured for inserting the intramedullary nail 102 through a nail insertion target in the cortex of the bone 104 and into the intramedullary canal. For example, the intramedullary nail 102 can be a trochanteric fixation nail for insertion into the intramedullary canal through a target location in the cortex, such as on the tip or slightly lateral to the tip of the greater trochanter. The insertion handle 108 can also be configured to couple with an aiming arm 110 that defines at least one aiming aperture 112 (or alternatively a channel) extending along an aiming trajectory or axis 114 that intersects a lateral channel or "locking hole" 116 of the intramedullary nail 102 generally in a lateral-to-medial direction. One or both of the insertion handle 108 and the aiming arm 110 can include an adjustment feature allowing adjustments of the position of the aiming arm 110 relative to the insertion handle 108, and thus also adjusting the trajectory 114 of the aiming aperture 112. For example, the trajectory 114 can be adjusted so as to be coincident with an axis of the trochanter.

The bone fixation system 100 includes a locking assembly 200 configured to extend through the aiming aperture 112 of the aiming arm 110 for inserting a fixation member 2 through the locking hole 116 of the intramedullary nail 102 and into engagement with bone, such as the far cortex thereof. In the illustrated embodiment, the aiming arm 110 is configured to guide insertion of the fixation member 2 through the femoral neck 105 and into the femoral head 107 along a trajectory 114 that intersects an apex 109 of the femoral head 107. The locking assembly 200 includes a guide sleeve 4 that is insertable through the aiming aperture 112 along the trajectory 114 and through which additional instruments, such as guide wires, wire guides, drill bits, drivers, inserters, and the like, can be guided and advanced to the bone 104 and/or to the intramedullary nail 102, including to and/or through the locking hole 116 thereof. It should be appreciated that an outer surface 6 of the guide sleeve 4 preferably has a geometry complimentary with that of an inner surface of the aiming arm 110 within the aiming aperture 112 so that the guide sleeve 4 is retained therein in a snug manner.

Figure 2:
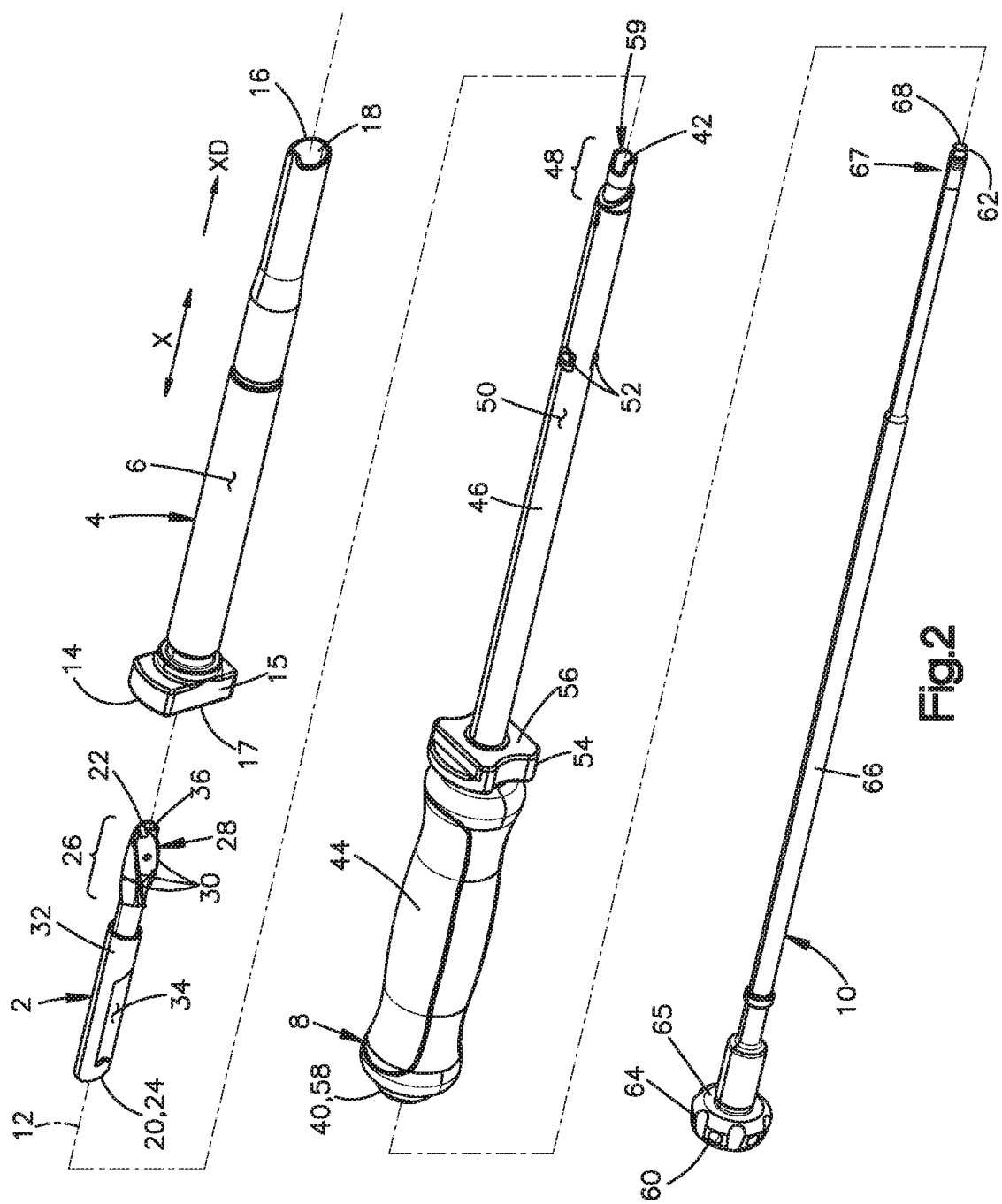
FIG. 2 is an exploded perspective view of a locking assembly of the bone fixation system illustrated in FIG. 1.

Referring now to FIG. 2, the locking assembly 200 can include the fixation member 2, the guide sleeve 4, an insertion instrument 8 for advancing the fixation member 2 through the guide sleeve 4, and a coupling instrument 10 for coupling the fixation member 2 to the insertion instrument 8. The guide sleeve 4 is elongate along a central axis 12 and has a proximal end 14 and a distal end 16 spaced from each other along a longitudinal direction X that is oriented along the central axis 12. The guide sleeve 4 defines an axial bore 18 that extends along the central axis 12 from the proximal end 14 to the distal end 16 along a distal direction XD oriented along the longitudinal direction X. The axial bore 18 can be centrally located in the guide sleeve 4 and can thus be referred to as a "central" bore 18. The guide sleeve 4 includes a proximal stop member, such as a flange 15, that defines a proximal surface 17 of the guide sleeve 4 at the proximal end 14 thereof.

The fixation member 2 has a proximal end 20 and a distal end 22 spaced from each other along the longitudinal direction X. The fixation member 2 includes a proximal mount 24 for mounting to the insertion instrument 8 and a head 26 spaced from the proximal mount 24 in the distal direction XD. The head 26 includes a bone engagement feature, such as a helical structure 28, for engaging bone as the fixation member 2 advances distally from the guide sleeve 4. The helical structure 28 can include a plurality of helical cutting blades 30 that extend helically about the central axis 12 and are configured to cut, bite, or otherwise drill through bone material, including cortical bone material and cancellous bone material. The fixation member 2 includes a locking member 32 configured to lockingly engage a complimentary locking member of the intramedullary nail 102. In the illustrated embodiment, the locking member 32 defines one or more outer locking surfaces 34 defining a geometry configured to engage a complimentary geometry of the complimentary locking member of the intramedullary nail 102, as described in more detail below. The fixation member 2 preferably defines a cannulation 36, such as for receiving a guide wire or other instrumentation and/or for allowing delivery of a material therethrough, such as augmentation material, such as cement, bone fill material, bone-growth inducing material, bone graft, and the like.

The insertion instrument 8 has a proximal end 40 and a distal end 42 spaced from each other along the longitudinal direction X. The insertion instrument 8 has a handle 44 at the proximal end 40 and an elongate insertion portion 46 that extends from the handle 44 in the distal direction XD to the distal end 42. The handle 44 is shaped to provide satisfactory purchase for the hand of an operator. The insertion portion 46 is configured to extend through the axial bore 18 of the guide sleeve 4 and includes a distal mount 48 at the distal end 42 for mounting to the proximal mount 24 of the fixation member 2. The distal mount 48 and the proximal mount 42 have complimentary geometries for transmitting axial and rotational forces from the insertion instrument 8 to the fixation member 2, as described in more detail below. The insertion portion 46 has an outer surface 50 that defines at least one follower member, such as at least one protrusion 52, that is configured to engage and follow a complimentary guide feature located within the axial bore 18 of the guide sleeve 4 to thereby guide movement of the insertion portion 46 (and the fixation member 2 mounted thereto) through the guide sleeve 4. Preferably, the at least one protrusion 52 includes a plurality of protrusions unevenly spaced from one another about the circumference of the outer surface 50 of the insertion portion 46. Engagement between the protrusions 52 and the complimentary guide features within the axial bore 18 of the guide sleeve 4 will be described in more detail below. The insertion instrument 8 includes a stop member, such as a flange 54, that defines a distal stop surface 56 configured to abut the proximal surface 17 of the guide sleeve 4 when the insertion portion 46 (and thus also the fixation member 2 mounted thereto) is at a maximum insertion depth relative to the guide sleeve 4. The insertion instrument 8 also has a proximal stop surface 58 located at the proximal end 40 thereof, and defines a cannulation 59 extending from the proximal end 40 to the distal end 42.

The coupling instrument 10 has a proximal end 60 and a distal end 62 spaced from each other along the longitudinal direction X. The coupling instrument 10 includes a proximal flange 64 at the proximal end 60 and an elongate portion 66 that extends from the proximal flange 64 in the distal direction XD to the distal end 62. The elongate portion 66 of the coupling instrument 10 is configured to extend through the cannulation 12 of the insertion instrument 8 such that a coupling feature, such as an externally threaded coupling portion 67 at the distal end 62, extends distally from the distal mount 48 of the insertion instrument 8 and engages a complimentary coupling feature, such as an internally threaded proximal portion of the fixation member 2, for coupling with the fixation member 2. The proximal flange 64 can have knurls or the like for facilitating rotation of the elongate portion 66 relative to the fixation member 2 so as to threadedly engage the externally threaded coupling portion 67 of the coupling instrument 10 with the internally threaded proximal portion of the fixation member 2, which can effectively draw the fixation member 2 proximally relative to the distal mount 48 of the insertion instrument 8 so that the proximal mount 24 of the fixation member 2 is fully seated to the distal mount 48, at which fully seated position the proximal and distal mounts 24, 48 are preferably rigidly engaged with one another. The coupling instrument 10, insertion instrument 8, and the fixation member 2 can be cooperatively configured such that a distal surface 65 of the flange 64 abuts the proximal stop surface 58 of the insertion instrument 8 when the proximal mount 24 is fully seated to the distal mount 48. The coupling instrument 10 preferably defines a cannulation 68, such as for receiving a guide wire or other instrumentation.

Referring now to FIGS. 3 through 5, the proximal mount 24 of the fixation member 2 can include a plurality of mounting formations. One such mounting formation can include one or more transverse surfaces 70 (also referred to herein as "landings" or "flats") that extend parallel with a transverse direction T perpendicular to the central axis 12. Another such mounting formation can include an additional flat, such as an inferior flat 71, as shown in FIG. 5, located opposite the one or more transverse surfaces 70. A yet another such mounting formation can include an axial abutment surface 72 generally facing in a proximal direction XP opposite the distal direction XD. An additional such mounting formation can include a proximal surface 74 at the proximal end 20 of the fixation member 2. As shown, the proximal surface 74 can be canted at an oblique angle relative to the central axis 12. The mounting formations 70, 71, 72, 74 of the proximal mount 24 can each be configured to engage complimentary mounting formations of the distal mount 48.

The fixation member 2 can optionally comprise two or more anchor bodies coupled together. For example, the fixation member 2 can include a distal anchor body 2a that defines the head 26 and a proximal anchor body 2b that defines the locking member 32 and the proximal end 20 of the fixation member 2. The proximal anchor body 2b can be tubular and can define a generally cylindrical outer surface 33. The proximal anchor body 2b can also be configured to receive a shank 76 of the distal anchor body 2a. The distal and proximal anchor bodies 2a, 2b can be configured for selective telescopic movement relative to each other. For example, the shank 76 of the distal anchor body 2a can include a compliant pawl 78 that is configured to engage at least one of a series of complimentary ratchet teeth 79 defined on or carried by an internal surface of the proximal anchor body 2b. Accordingly, the pawl 78 and ratchet teeth 79 can be employed to selectively adjust the axial length L1 of the fixation member 2 prior to engaging the proximal mount 24 to the distal mount 48. It should be appreciated that the fixation member 2 can be configured as described in U.S. Pat. No. 8,808,293, issued Aug. 19, 2014, and entitled "TROCHANTERIC FEMORAL NAIL AUGMENTABLE" ("the '293 Reference"), the entire disclosure of which is incorporated herein by this reference. As shown, the distal anchor body 2a can define the transverse flats 70 and the axial abutment surface 72, while the proximal anchor body 2b can define the proximal surface 74 of the fixation member 2.

The helical cutting blades 30 of the head 26 can extend at a helix angle A1 measured with respect to the central axis 12. helically about the central axis 18 and can also define a pitch along the longitudinal direction X. The head 26 can also define one or more side ports 38 in fluid communication with the cannulation 36. The one or more side ports 38 can be configured to deliver material, such as any of the augmentation materials described above, from the head 26 in one or more respective radial directions R perpendicular to the central axis 12.

Figure 6:
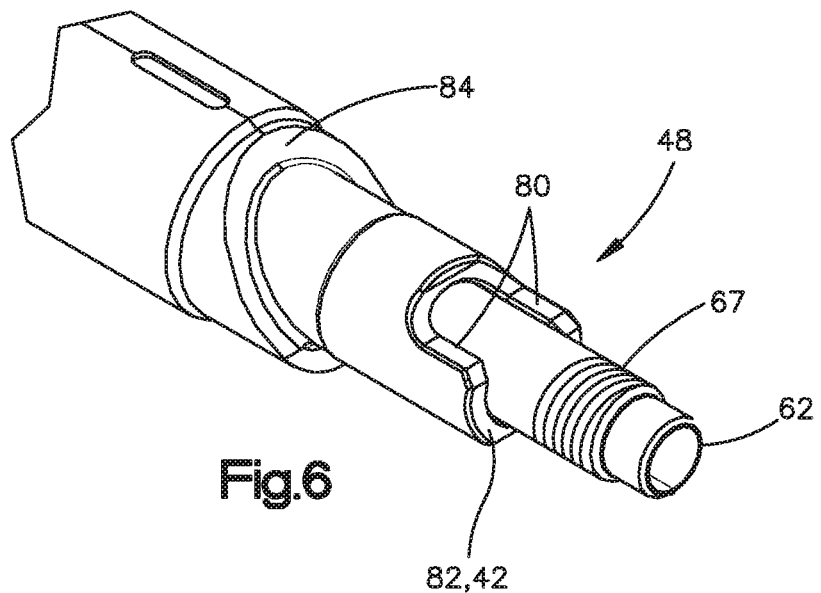
FIG. 6 is a perspective view of a distal mount of an insertion instrument illustrated in FIG. 2.
Figure 7:
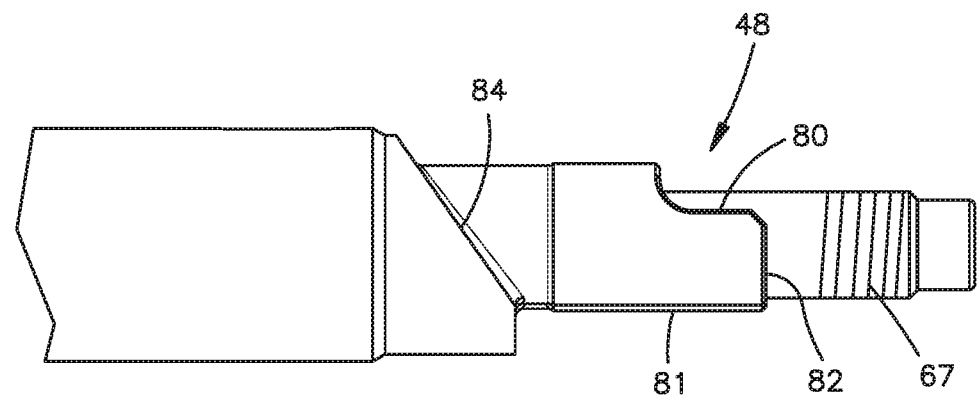
FIG. 7 is a side plan view of the distal mount illustrated in FIG. 6.

Referring now to FIGS. 6 through 8, the distal mount 48 of the insertion instrument 8 can include a plurality of mounting formations complimentary with those of the proximal mount 24 of the fixation member 2. For example, the distal mount 48 can include one or more transverse surfaces or flats 80 (also referred to herein as "landings") that extend parallel with the transverse direction T and are configured to oppose and abut the transverse flats 70 of the fixation member 2. The distal mount can also include an inferior flat 81 that also extends parallel with the transverse direction T and is configured to oppose and abut the inferior flat 71 of the fixation member 2. The distal mount 48 can also include a distal axial abutment surface 82 generally facing in the distal direction XD and configured to engage the proximal axial abutment surface 72 of the fixation member 2. The distal axial abutment surface 82 can define the distal end 42 of the insertion instrument 8. The distal mount 48 can further include a distal shoulder surface 84 configured to face the proximal surface 74 of the fixation member 2. The distal shoulder surface 84 is preferably canted at an oblique angle equivalent to that of the proximal surface 74. As shown in FIGS. 6 and 7, the externally threaded coupling portion 67 at the distal end 62 of the coupling instrument 10 extends distally from the distal mount 48 for engaging a complimentary internally threaded proximal portion of the fixation member 2 in a manner drawing the mounting formations 70, 71, 72, of the fixation member 2 into fully seated engagement with the mounting formations 80, 81, 82, of the insertion instrument 8, as shown in FIG. 8. The engaged transverse flats 70, 80 and 71, 81 transmit rotational forces to the fixation member 2 and the engaged axial abutment surfaces 72, 82 transmit axial forces to the fixation member 2, collectively providing a rigid, sturdy coupling, which is critical for proper alignment and locking engagement between the one or more outer locking surfaces 34 of the fixation member 2 and the complimentary locking member of the intramedullary nail 102. The rigid, sturdy coupling is also favorable for fine adjustability of the axial position of the fixation member 2 relative to the guide sleeve 4 (and thus also relative to the intramedullary nail 102 and the bone 104).

Figure 9B:
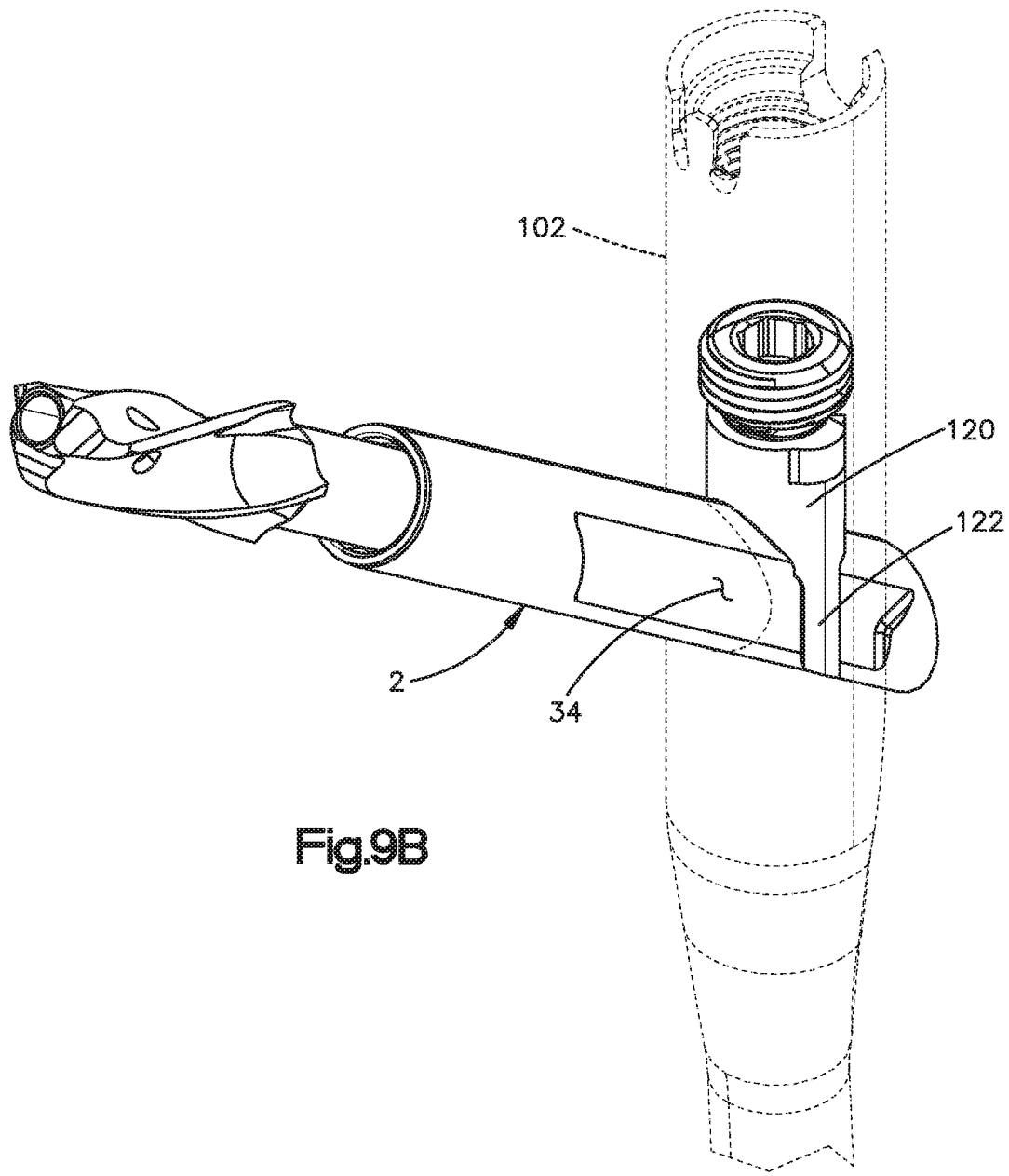
FIG. 9B is a perspective view of the fixation member shown in FIG. 9A engaged with a locking member of the intramedullary nail illustrated in FIG. 1.

As shown in FIG. 9A, the fixation member 2 can define a pair of outer locking surfaces 34 that are opposite each other along the transverse direction T. The outer locking surfaces 34 can be recessed from the generally cylindrical outer surface 33, such that the proximal anchor body 2b defines retention shoulders 35 at proximal and distal ends of the outer locking surfaces 34. As shown in FIG. 9B, the locking member of the intramedullary nail 102 can be a locking prong 120 that has an arm and is configured to advance within a central passage of the intramedullary nail 102 so that the arm engages one of the outer locking surfaces 34 of the fixation member 2, particularly in a form-fitting fashion, such that the arm abuts the respective retention shoulder 35 of the fixation member 2 should the fixation member 2 migrate along the central axis 12 after locking with the intramedullary nail 102. The retention shoulders 35 are configured for engaging the locking member of the intramedullary nail 102 in a manner impeding migration of the fixation member 2 along the medial-lateral direction. In other embodiments, the locking prong 120 can have a pair of opposed arms 122 that are configured to straddle the outer locking surfaces 34 of the fixation member 2.

Referring now to FIGS. 10 through 12, the guide sleeve 4 comprises a sleeve body 5 that defines the proximal and distal ends 14, 16, the outer surface 6, and the axial bore 18. The sleeve body 5 can also define the flange 15. The sleeve body 5 is preferably a monolithic body. The sleeve body 5 defines an internal surface 90 that defines the axial bore 18. The sleeve body 5 also defines at least one guide channel 92 that is recessed radially outwardly from the internal surface 90 and extends between the proximal and distal ends 14, 16 of the sleeve body 5. The at least one guide channel 92 is configured to guide movement of the fixation member 2 as it advances through the sleeve body 5. The at least one guide channel 92 includes a helical proximal portion 92a and a linear distal portion 92b that extends from the helical proximal portion 92 toward the distal end 16 of the sleeve body 5. The helical proximal portion 92a is configured to rotate the fixation member 2 about the central axis 12 as the fixation member 2 advances through bone material distally of the guide sleeve 4, thereby providing favorable engagement between the helical blades 30 of the head 26 and the bone material through which it travels. The linear distal portion 92b of the guide channel 92 is configured to provide precise, fine-adjustability of the axial position of the fixation member 2 relative to the bone material, such as the spacing between the distal end 22 of the fixation member 2 and the apex 109 of the femoral head 107, by way of a non-limiting example. The fine-adjustability of the axial position of the fixation member 2 is described in more detail below.

As shown, the at least one guide channel 92 can include a plurality of guide channels, which are spaced from one another about a circumference of the internal surface 90. In the illustrated embodiment, the plurality of guide channels 92 includes three (3) guide channels 92. The guide channels 92 are configured to receive the corresponding follower member of the insertion instrument 8, such as the protrusions 52 extending radially outwardly from the outer surface 50 thereof. The guide channels 92 are configured to guide movement of the protrusions 52 and thus also of the elongate insertion portion 46 as it advances through the axial bore 18 of the guide sleeve 4. Preferably, the guide channels 92 are unevenly spaced from one another about the circumference of the internal surface 90 in a manner corresponding to the uneven spacing of the protrusions 52 about the circumference of the outer surface 50 of the insertion portion 46 of the insertion instrument 8. In this manner, the protrusions 52 of the insertion instrument 8 will only fit within their associated guide channels 92, ensuring that the fixation member 2 is in the desired orientation about the central axis 12 when the protrusions 52 reside in the linear distal portions 92b of the guide channels 92. It should be appreciated that, in other embodiments, the sleeve body 5 can define one (1), two (2), four (4), five (5), six (6), or more than six guide channels 92, each of which can be configured to receive a corresponding follower member of the insertion instrument 8.

The helical proximal portion 92a of each guide channel 92 defines a helix angle A2 relative to the central axis 12, which helix angle A2 is preferably equivalent to the helix angle A1 of the helical cutting blades 30. Thus, as the insertion instrument 8 advances through the guide sleeve 4, the engagement between the protrusions 52 and the helical proximal portions 92a of the guide channels 92 will substantially cause the helical blades 30 of the head 26 to engage bone material primarily by a favorable compacting mechanism as opposed to a shearing mechanism, which compacting mechanism provides the helical blades 30 with self-channeling functionality and provides enhanced fixation. The helix angles A1, A2 can be in a range of about 5 degrees to about 60 degrees, and more particularly in a range of about 10 degrees to about 30 degrees, and more particularly in a range of about 15 degrees to about 20 degrees. The helix angle A2 of the helical proximal portion 92a of the guide channel 92 is preferably constant along the axial length of the helical proximal portion 92, although in other embodiments the helix angle can vary, such as to provide a measure bone compression along the insertion trajectory.

The linear distal portion 92b of each guide channel 92 extend parallel to the central axis 12 of the guide sleeve 4. The linear distal portion 92b of the guide channel 92 defines an axial length L2, which is preferably 4.0 mm or greater, and can be 5.0 mm or greater, and can further be in a range of about 4.0 mm and about 20 mm.

Referring now to FIG. 13, the distal end 22 of the fixation member 2 is shown at a first insertion position P1 relative to the guide sleeve 4, at which position the followers 52 of the insertion instrument 8 are located near proximal ends of the helical proximal portions 92a of the guide channels 92. From the first insertion configuration P1, a surgeon can advance the insertion instrument 8 carrying the fixation member 2 distally through the central bore 18 by impacting the proximal surface 58 of the insertion instrument 8, such as with an impaction hammer, until the followers 52 are guided to a second insertion position P2.

Referring now to FIG. 14, when the fixation member 2 is at the second insertion position P2, the followers 52 are located at an interface 94 or transition between the helical proximal portion 92a and the linear distal portion 92b of the guide channel 92. It should be appreciated that at the second insertion position, the outer locking surfaces 34 of the fixation member 2 are properly oriented for engagement with the locking prong of the intramedullary nail 102. Thus, if the axial position of the fixation member 2 relative to the intramedullary nail 102 is sufficient at the second insertion position P2, the surgeon can opt to forego further axial advancement of the fixation member 2, and can instead move the locking member of the intramedullary nail 102 into locking engagement with the outer locking surfaces 34 of the fixation member 2.

Referring now to FIG. 15, if further axial advancement of the fixation member 2 is desirable or necessary, such as for ensuring proper locking with the locking member of the intramedullary nail 102, and/or achieving a better tip-apex distance, the surgeon can utilize the linear distal portions 92b of the guide channels 92 for incremental insertion, such as by applying a few impactions, or even a single impaction, to the proximal surface 58 of the insertion instrument 89 while observing visual indicia of the of the axial location of the fixation member 2. Such visual indicia can include fluoroscopy. For example, at last a part of the fixation member 2 can be constructed of a radiopaque material, or can carry one or more radiopaque markers, for observation under fluoroscopy. Additionally or alternatively, visual indicia can include markings, such as graduated hash marks on the outer surface 50 of the insertion portion 46 of the insertion instrument 8 or, as shown in FIG. 16, a raised boss 57 extending distally from the flange 56 at a predetermined length L3, by way of non-limiting examples. In the embodiment shown in FIG. 16, the raised boss 57 indicates when the insertion portion 46 of the insertion instrument 8 (and thus also the fixation member 2 mounted thereto) is within the predetermined length L3 from the maximum insertion depth relative to the guide sleeve 4. The predetermined length L3 can correspond to the axial length L2 of the linear distal portions 92b of the guide channels 92 so that the raised boss 57 can indicate when the protrusions 52 are within the linear distal portions 92b. The foregoing steps of incremental insertion can be repeated as needed for fine adjustability of the fixation member 2 insertion, optionally until the followers 52 are located at distal termini of the linear distal portions 92b of the guide channels 92, at which location the distal end 22 of the fixation member 2 is at a third, maximum insertion position P3.

The axial length L2 of the linear distal portions 92b of the guide channels 92 is particularly advantageous because the fixation members of intramedullary nailing systems are often provided in discrete increments of length L1, such as 5.0 mm increments, for example. Thus, if any combination of patient anatomy, intramedullary nail insertion position, and bone fragmentation, compression, or distraction requires a fixation member length L1 between such a 5.0 mm increment, the physician may have to choose between a fixation member length L1 that can be as up to 5.0 mm longer or shorter than the desired length L1. Such an overlength or underlength fixation member may present challenges with proper engagement with the complimentary locking member of the intramedullary nail 102. For example, to ensure proper alignment between the outer locking surfaces 34 of the fixation member 2 and the arm 122 of the locking prong 120, the axial position and the rotational orientation of the fixation member 2 must align with the arm 122 of the locking prong 120, otherwise the arms risk not engaging the outer locking surfaces 34, which can leave the fixation member 2 free to slide along the locking hole 106, which can lead to migration of the fixation member 2 along the medial-lateral direction. Without the linear distal portion 92b of the guide channel 92, the surgeon must advance the fixation member 2 to the full length of the helical guide channel so as to ensure proper engagement with the locking prong, even if such full advancement results in a shorter than desired tip-apex distance. The linear distal portion 92b of the guide channel 92 maintains the orientation of the fixation member 2 for proper engagement with the locking prong 120, while also allowing the surgeon to incrementally advance the fixation member to an optimal tip-apex distance.

Although the disclosure has been described in detail, it should be understood that various changes, substitutions, and alterations can be made herein without departing from the spirit and scope of the invention as defined by the appended claims. For example, features of the various embodiments described herein can be incorporated into one or more and up to all of the other embodiments described herein. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A bone fixation system for use with an intramedullary nail, comprising:
   a guide sleeve elongate along a central axis and including
      a sleeve body configured to be held in position relative to a bone by an aiming arm, the sleeve body including an internal surface that defines a bore extending along the central axis to a distal end of the sleeve body, the sleeve body defining at least one guide channel that is recessed radially outwardly from the internal surface and includes a helical proximal portion and a linear distal portion, wherein the linear distal portion extends from the helical proximal portion toward the distal end and is parallel with the central axis;
   a fixation member configured to extend through the bore of the guide sleeve, the fixation member having a proximal mount and a distal head spaced from the proximal mount in a distal direction, the distal head having a helical structure configured to engage bone; and an instrument having an elongate portion that includes a distal mount configured to couple with the proximal mount of the fixation member, such that, when coupled, the instrument is configured to advance the fixation member through the bore of the guide sleeve, the elongate portion having an outer surface and at least one protrusion extending radially outward from the outer surface, wherein the at least one protrusion is configured to extend within and follow the at least one guide channel as the elongate portion advances through the bore of the guide sleeve so as to control an axial position of the fixation member relative to the guide sleeve.

2. The bone fixation system of claim 1, wherein the linear distal portion of the at least one guide channel defines an axial length of at least 4.0 mm.

3. The bone fixation system of claim 1, wherein the guide sleeve, the instrument, and the fixation member are cooperatively configured such that the fixation member 1) advances in the distal direction and rotates about the central axis as the at least one protrusion follows the helical proximal portion of the at least one guide channel and 2) advances in the distal direction substantially without rotating about the central axis as the at least one protrusion follows the linear distal portion of the at least one guide channel.

4. The bone fixation system of claim 3, wherein the instrument has a proximal end and an impaction surface at the proximal end thereof, wherein the impaction surface is configured for receiving impactions from an impaction member to thereby advance the at least one protrusion along the helical proximal portion and at least a portion of the linear distal portion of the at least one guide channel.

5. The bone fixation system of claim 1, wherein the at least one guide channel comprises a plurality of guide channels defined by the internal surface of the guide sleeve, and the plurality of guide channels are substantially equidistantly spaced from one another about a circumference of the internal surface.

6. The bone fixation system of claim 5, wherein the at least one protrusion comprises a plurality of protrusions extending radially outward from the outer surface of the elongate portion of the instrument, the plurality of protrusions are unevenly spaced from one another about a circumference of the outer surface, and the plurality of protrusions are configured to respectively extend within and follow the plurality of guide channels.

7. The bone fixation system of claim 1, wherein the fixation member defines an outer locking surface that is configured to engage a complimentary locking member of the intramedullary nail, such that when the outer locking surface is engaged with the locking member, the fixation member is prevented from rotating relative to the intramedullary nail bout the central axis.

8. The bone fixation system of claim 7, wherein the outer locking surface is a first outer locking surface, and the fixation member defines a second outer locking surface opposite the first outer locking surface along a transverse direction perpendicular to the central axis, and the second outer locking surface is configured to abut a complimentary locking surface of the intramedullary nail.

9. The bone fixation system of claim 8, wherein:
the first and second outer locking surfaces are each planar and are parallel with one another, and the at least one guide channel and the fixation member are cooperatively configured such that the first and second outer locking surfaces each remain parallel with a central nail axis of the intramedullary nail while the at least one protrusion of the instrument resides within the linear distal portion of the at least one guide channel.

10. The bone fixation system of claim 1, wherein the helical structure of the distal head defines a helix angle that is substantially equivalent to a helix angle defined by the helical proximal portion of the at least one guide channel.

11. The bone fixation system of claim 1, wherein the outer surface of the elongate portion of the instrument includes visual indicia for indicating an axial distance by which a distal end of the distal head extends from a distal end of the guide sleeve.

12. The bone fixation system of claim 1, wherein at least the distal head of the fixation member is constructed of a material that is radiopaque for providing a visual indication under radioscopy of an axial distance between a distal end of the distal head and an apex of a portion of the bone.

13. A guide sleeve for use in anchoring a fixation member to an intramedullary nail and to bone, comprising:
a sleeve body elongate along a central axis, the sleeve body having an internal surface that defines a bore extending along the central axis to a distal end of the sleeve body, the sleeve body defining a plurality of guide channels that are each recessed radially outwardly from the internal surface, each of the plurality of guide channels including a helical proximal portion and a linear distal portion that extends from the helical proximal portion toward the distal end and being parallel with the central axis, wherein the bore is configured to receive an instrument, such that complimentary followers of the instrument extend into the guide channels, respectively, so that the instrument drives the fixation member through the bore and subsequently through the intramedullary nail and into the bone.

14. The guide sleeve of claim 13, wherein the linear distal portion of each of the guide channels defines an axial length of at least 4.0 mm.

15. The guide sleeve of claim 13, wherein the plurality of guide channels comprise three guide channels spaced from one another about a circumference of the internal surface.

16. A method of affixing an intramedullary nail within an intramedullary canal of a bone, the method comprising:
advancing a guide sleeve through a complimentary aperture in an aiming arm attached to the intramedullary nail until a distal end of the guide sleeve contacts an outer cortex of the bone along a trajectory defined along a central axis of the guide sleeve such that the central axis intersects a lateral channel of the intramedullary nail;
inserting an instrument through a central bore of the guide sleeve such that external followers of the instrument extend within respective channels defined within an internal surface of the guide sleeve within the central bore, wherein proximal portions of the channels extend helically along the internal surface;
impacting a proximal surface of the instrument with a hammer, thereby moving the external followers along the proximal portions of the channels, thereby 1) advancing a fixation member, coupled to a distal end of the instrument, axially along the central axis, and 2) simultaneously rotating the fixation member about the central axis, wherein the impacting step causes a helical structure of the fixation member to advance through the lateral channel of the intramedullary nail and subsequently engage bone; and further impacting the proximal surface with the hammer, thereby moving the external followers into distal linear portions of the channels that extend parallel with the central axis, thereby advancing the fixation member axially into further engagement with the bone substantially without rotating the fixation member about the central axis.

17. The method of claim 16, further comprising, during at least one of the impacting and further impacting steps, observing visual indicia representing axial spacing between a distal end of the fixation member and the bone.

18. The method of claim 17, further comprising, during the observing step, terminating the further impacting step while the external followers are proximally spaced from distal termini of the distal linear portions of the channels.

19. The method of claim 17, wherein the visual indicia comprises graduated hash marks on an outer surface of the instrument or a raised boss extending from the outer surface of the instrument.

20. The method of claim 17, wherein the visual indicia comprises at least one radiopaque portion of the fixation member, and the observing step comprises viewing the at least one radiopaque portion under fluoroscopy.

* * * * *